United States Patent [19]

Koga et al.

[11] 4,297,499

[45] Oct. 27, 1981

[54] NOVEL DISUBSTITUTED DICHLOROSILANE AND METHOD FOR PRODUCING SAME

[75] Inventors: Isao Koga, Yokohamashi; Yohji Terui, Chibashi; Masuhito Ohgushi; Tohru Kitahara, both of Minamatashi, all of Japan

[73] Assignee: Chisso Corporation, Osaka, Japan

[21] Appl. No.: 895,332

[22] Filed: Apr. 11, 1978

[30] Foreign Application Priority Data

Apr. 12, 1977 [JP] Japan .................................. 52-41686
Jun. 30, 1977 [JP] Japan .................................. 52-78186
Jan. 24, 1978 [JP] Japan .................................. 53-6584

[51] Int. Cl.$^3$ .............................................. C07F 7/08
[52] U.S. Cl. .................... 556/465; 556/489; 556/479
[58] Field of Search ............... 260/448.2 E, , 448.2 R; 556/489, 465

[56] References Cited

U.S. PATENT DOCUMENTS

| 2,823,218 | 2/1958 | Speier et al. | 260/448.2 E |
| 3,159,601 | 12/1964 | Ashby | 260/448.2 E X |
| 3,231,594 | 1/1966 | Speier | 260/448.2 E |
| 3,546,266 | 12/1970 | Coffey | 260/448.2 E |
| 3,631,086 | 12/1971 | Seyfried et al. | 260/448.2 E |
| 3,856,837 | 12/1974 | Chandra | 260/448.2 E X |
| 3,864,372 | 2/1975 | Svoboda et al. | 260/448.2 E |
| 3,867,343 | 2/1975 | Garden | 260/448.2 E X |
| 3,907,850 | 9/1975 | Capka et al. | 260/448.2 E |
| 3,907,852 | 9/1975 | Oswald et al. | 260/448.2 E X |
| 3,992,427 | 11/1976 | Chandra et al. | 260/448.2 E |

OTHER PUBLICATIONS

Bazant et al., "Organosilicon Compounds", vol. 2, Part 1, Academic Press, N.Y. (1965), p. 275.

Primary Examiner—Paul F. Shaver
Attorney, Agent, or Firm—Fred Philpitt

[57] ABSTRACT

Novel disubstituted dichlorosilane compounds which have two different specified substituents and are necessary as monomers for preparing special silicone resin are provided and a method for producing same without accompaniment of by-product production is also provided.

11 Claims, 9 Drawing Figures

NOVEL DISUBSTITUTED DICHLOROSILANE AND METHOD FOR PRODUCING SAME

DESCRIPTION OF THE INVENTION

This invention relates to a novel disubstituted dichlorosilane and a method for producing the same.

Disubstituted dichlorosilane compounds are important as bifunctional monomers for polysiloxanes (hereinafter referred to as monomers) but the monomers which have been heretofore found have been mostly those in which substituted radicals thereof are methyl or phenyl and two substituent radicals are same. With the recent development of silicone resin industry, silicone resins having special properties have become necessary and thus disubstituted dichlorosilane compounds which have not been known have become necessary. For example, those having two different substituent radicals one of which is a cyclic group, those containing different kinds of alkyl groups having a large number of carbon atoms, etc. are mentioned. The dialkyldichlorosilanes heretofore existing are mostly those in which two alkyl groups are same or one of them is methyl. Among dialkyldichlorosilanes heretofore commercially used, those containing same alkyl groups are only dimethyl or diethyl dichlorosilanes and those containing different alkyl groups are only methyl, ethyl-; methyl, hexyl-; methyl, decyl-dichlorosilanes. In addition, such compounds as $C_2H_5SiCl_2(n\text{-}C_4H_9)$ [Chemical Abstracts, vol. 50, page 7844e (herein abbreviated as C.A. 50, 7844e)], $C_2H_5SiCl_2CH_2CH(CH_3)_2$ [C.A. 50, 13726f], $C_2H_5SiCl_2(n\text{-}C_6H_{13})$ [C.A. 62, 2795c], $C_2H_5SiCl_2(n\text{-}C_7H_{15})$ [C.A. 76, 3055b], $C_3H_7SiCl_2(n\text{-}C_6H_{13})$ [C.A. 73, 13777r] are found in the literatures. As disubstituted dichlorosilanes having a cyclic group, only such compounds as $C_2H_5SiCl_2(CH_2CH_2Ph)$ [C.A. 68, 44645X], $C_2H_5SiCl_2\{CH(CH_3)Ph\}$ [C.A. 54, 22435C] are found in the literature besides phenyldichlorosilane.

As production methods of disubstituted dichlorosilanes, a method in which monosubstituted dichlorosilane represented by the formula $RHSiCl_2$ (wherein R is an organic radical) is prepared and H connected with Si of this compound is substituted by other substituent radical, can be thought of, but the production of this compound $RHSiCl_2$ is accompanied with a large amount of by-product, involves danger in processing because of the use of ether and cannot be regarded as commercially feasible process. Further Rochow method has been known but it is not suitable as a method for producing disubstituted dichlorosilane containing different organic radicals.

On the other hand, various kinds of chlorosilanes can be obtained from silicon and hydrochloric acid. Among them, the utilization of trichlorosilane and research relating to it are most abundant. On the contrary, it is the actual state of the art that there is almost no investigation made with regard to the utilization of dichlorosilane.

It is an object of the present invention to provide novel disubstituted dichlorosilanes containing different kinds of substituent radicals, which have not been known in the past. It is another object of the present invention to provide a novel method for producing disubstituted dichlorosilanes from dichlorosilanes which are not accompanied with the drawbacks of the conventional methods such as those above-mentioned.

The disubstituted dichlorosilane compounds of the present invention have the following general formula (I)

wherein R' is an alkyl group having 2 or 3 carbon atoms and R" is an alkyl group having 8 to 20 carbon atoms; or R' is an alkyl group having 4–20 carbon atoms and R" is an alkyl group having 5–20 carbon atoms and R'≠R"; or R' is an alkyl group having 2–20 carbon atoms or phenethyl group and R" is a cyclohexyl group.

More specifically, the compounds of the present invention firstly include dialkyldichlorosilane compounds having the general formula (I) in which R' is an alkyl having 2–3 carbon atoms and R" is an alkyl having 8–20 carbon atoms such as n-ethyl.n-octyldichlorosilane; n-propyl.n-octyldichlorosilane; n-ethyl.dodecyldichlorosilane; n-propyl.dodecyldichlorosilane; n-ethyl.octadecyldichlorosilane; n-propyl.octadecyldichlorosilane, etc.

The compounds of the present invention secondly include dialkyldichlorosilane compounds having the general formula (I) in which R' is an alkyl group having 4–20 carbon atoms and R" is a different alkyl group having 5–20 carbon atoms from R', and compounds having R' and R" the number of carbon atoms of which are different by 6 or more are preferable for the purpose of the present invention. As concrete names of the compounds, n-hexyl.dodecyldichlorosilane; n-hexyl.octadecyldichlorosilane; n-dodecyl.octadecyldichlorosilane; n-octyl.octadecyldichlorosilane and the like can be mentioned.

The compounds of the present invention thirdly include alkylcyclohexyldichlorosilane compounds having the general formula (II)

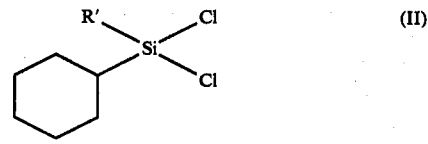

wherein R' is an alkyl group having 2–20 carbon atoms. As concrete compounds, there can be mentioned ethylcyclohexyldichlorosilane; propylcyclohexyldichlorosilane; butylcyclohexyldichlorosilane; isobutylcyclohexyldichlorosilane; pentylcyclohexyldichlorosilane; isoamylcyclohexyldichlorosilane; hexylcyclohexyldichlorosilane; heptylcyclohexyldichlorosilane; octylcyclohexyldichlorosilane; nonylcyclohexyldichlorosilane; decylcyclohexyldichlorosilane; undecylcyclohexyldichlorosilane; dodecylcyclohexyldichlorosilane; hexadecylcyclohexyldichlorosilane; octadecylcyclohexyldichlorosilane; eicosylcyclohexyldichlorosilane; and the like.

The compounds of the present invention fourthly include cyclohexylphenethyldichlorosilane represented by the general formula (III)

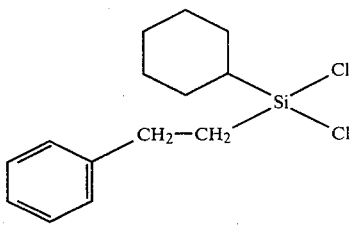

(III)

The production method of the present invention for the disubstituted dichlorosilane represented by the formula (I) comprises reacting dichlorosilane with an α-olefin having 2~20 carbon atoms, cyclohexene or styrene in the presence of as a catalyst, a complex of a transition metal (the 8th group) and a phosphine derivative, ruthenium chloride or chloroplatinic acid to form a mono-substituted dichlorosilane compound having the general formula R°HSiCl₂ (wherein R° is an alkyl group having 2~20 carbon atoms, cyclohexyl or phenethyl in the first step and subjecting resulting monosubstituted dichlorosilane compound to addition reaction in the presence of chloroplatinic acid catalyst at a temperature of 30°-150° C. with an α-olefin having 2~20 carbon atoms (the number of carbon atoms being different from that of R°) or cyclohexene (excepting the case of R° being alkyl or cyclohexyl), in the second step.

As catalysts, complexes of transition metals (the 8th group of the periodical table) and phosphine derivatives such as RhH(PPh₃)₄; RhH(CO)(PPh₃)₃; RhCl(CO)(PPh₃)₂; RhCl(PPh₃)₃; RuCl₂(PPh₃)₃; RuHCl(PPh₃)₃[C₆H₆]; RuHCl(PPh₃)₃C₆H₅CH₃; RuH₃(PPh₃)₃[Si(OCH₃)₃]; RuH₃(PPh₃)₃—[Si(OCH₃)₂Ph]; RuH(PPh₃)₃[Si(C₂H₅)₂Cl]; RuH₂(PPh₃)₄; NiCl₂(PPh₃)₂; PdCl₂(PPh₃)₂; Pd(PPh₃)₄; Pt(PPh₃)₄, etc., RuCl₃.3H₂O and H₂PtCl₆.6H₂O can be mentioned.

The concentration of catalyst used in the production method of the present invention is in the range of 1~10⁻¹⁵ mol % preferably 1~10⁻⁸ mol % per dichlorosilane in the first step reaction and 1~10⁻¹⁵ mol % preferably 1~10⁻⁸ mol % per monosubstituted dichlorosilane in the second step reaction.

The reaction temperature is in the range of 30°~200° C. preferably 30°~150° C. in the first step reaction and preferably 30°~150° C. in the second step reaction.

The reaction time is in the range of 0.1~60 hours.

Description of production method will be made more concretely.

For producing dialkyldichlorosilanes of the first and the second compounds of the present invention, dichlorosilane and a necessary α-olefin compound are reacted in the presence of a complex of a phosphine derivative and a transition metal as catalyst at a temperature of 30°~200° C., preferably 30°~110° C. for 0.1~60 hours in the first step and the resulting reaction solution is distilled after reaction to obtain an alkyldichlorosilane compound. This compound and a necessary α-olefin which is different from the above-mentioned α-olefin are heated at a temperature of 30°-150° C. in the presence of H₂PtCl₆ catalyst to carry out the second step reaction to obtain a dialkyldichlorosilane.

For producing alkylcyclohexyldichlorosilane compounds of the third group represented by the second formula, dichlorosilane and cyclohexene are reacted in the presence of H₂PtCl₆.6H₂O as a catalyst in the first step reaction and the resulting cyclohexyldichlorosilane and an α-olefin compound are reacted in the presence of the above-mentioned catalyst in the second step reaction to obtain an alkylcyclohexyldichlorosilane represented by the formula (I). It is preferable to use a reaction temperature of 30°-110° C. both for the first step reaction and the second step reaction. There is no limitation to the ratio of dichlorosilane and cyclohexene in the reaction, but in case the second step reaction is to be carried out without subjecting the product of the first step reaction, cyclohexyldichlorosilane to purification treatment such as distillation and separation, it is preferable to use cyclohexene in an equimolar ratio or more relative to dichlorosilane.

Fourthly, cyclohexylphenethyldichlorosilane can be obtained by the addition reaction of cyclohexene to phenethyldichlorosilane or the addition reaction of styrene to cyclohexyldichlorosilane but preferable production method will be as follows:

dichlorosilane and styrene are reacted in the presence of as a catalyst, a complex of a transition metal and a phosphine derivative at a temperature of 30°~150° C. for 0.1~60 hours to synthesize phenethyldichlorosilane and this phenethyldichlorosilane and cyclohexene are reacted in the presence of chloroplatinic acid catalyst at a temperature of 80°~150° C. for 5~20 hours.

The compounds of the present inventions are compounds which have not been known heretofore and can be used as monomers for polysiloxanes for silicone rubber, silicone oil, silicone grease, silicone varnish and the like.

The polysiloxanes which are now widely used, are mostly lower-dialkylpolysiloxanes containing methyl or ethyl group. These lower-dialkylpolysiloxanes have drawbacks in the points that the compatibility with various kinds of polymers and solvents is poor, low temperature properties are inferior, boundary lubricating property is poor in case of use as a lubricating oil, coating property for paintings is inferior when it is used as a releasing agent and on this account their application fields are rather limitative.

The polysiloxane derived from the dialkyldichlorosilane compounds of the present invention can be improved in their compatibility with other polymers and solvents by properly selecting alkyl groups in R' and R" of the formula (I).

This fact is particularly advantageous when said polysiloxane is to be used for paintings. Further, it is possible to improve the low temperature properties of said polysiloxane notably at the same time, hence it is expected that usefulness of this material increases further in future from the point of resource development in colder territories. Further since this material is superior in compatibility with other lubricating oils, it provides desirable advantages to the characteristic properties and uses of lubricating oils. Further when it is used as a releasing agent, it is possible to obtain polysiloxane superior in coating properties compared with conventional products. Further it is also used as a plasticizer, etc.

From the alkylcyclohexyldichlorosilane compounds and cyclohexylphenethyldichlorosilane of the present invention, it is possible to prepare polysiloxanes which have not been known in the past by being subjected to hydrolysis followed by polycondensation or by being subjected to copolycondensation with a bifunctional polysiloxane monomer which has been heretofore known. They are very useful in the improvement of silicone oils, rubbers, varnishes which are widely used in the fields of electrical insulating materials, lubricating oils, water repellent, paintings, releasing agents.

The feature of the production method of the present invention is the use of dichlorosilanes which have not been used in the past, as raw materials and capability of producing useful disubstituted dichlorosilane compounds which have not been known from dichlorosilane with an extremely high yield. Particularly, due to the usability of the same catalyst in the first and second step reactions in the production of cyclohexylalkyldichlorosilanes, it is possible to carry out the second step reaction without purification of cyclohexyldichlorosilane as the intermediate product and in this regard this is an extremely advantageous commercial production method.

The compounds of the present invention and the method for producing same will be described more concretely by way of specific examples which are offered for the purpose of illustration but not for the purpose of limitation.

DESCRIPTION OF DRAWINGS

The infrared spectra and NMR spectra of the compounds of Examples are shown in FIGS. 1-9 as shown in the following table.

TABLE

Figure 1:
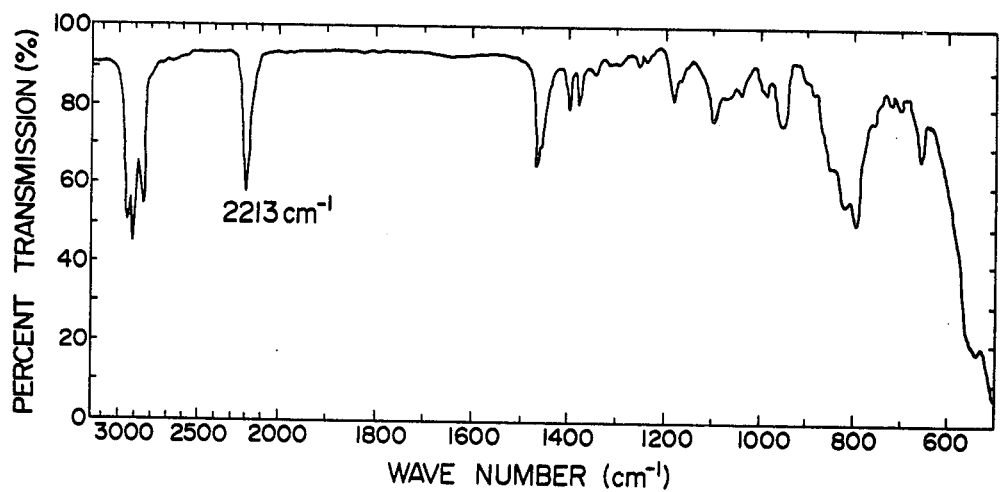
Figure 2:
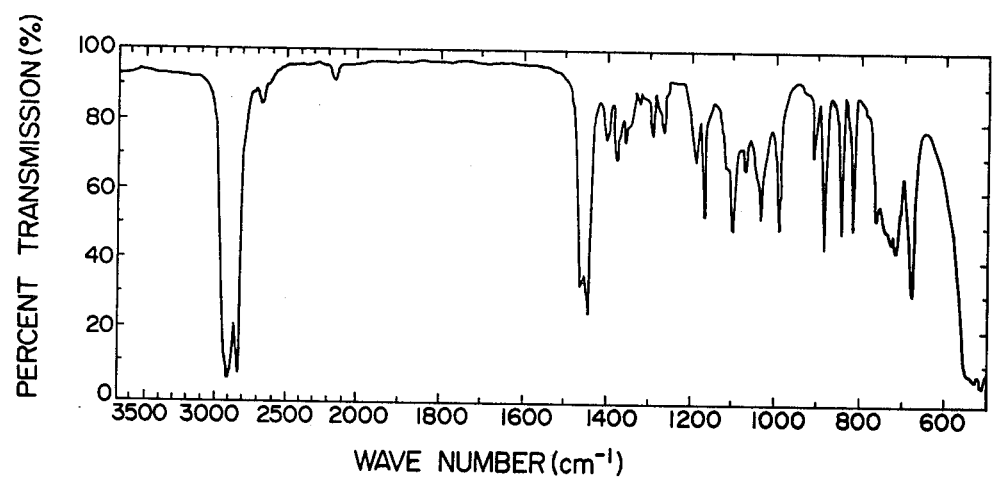
Figure 3:
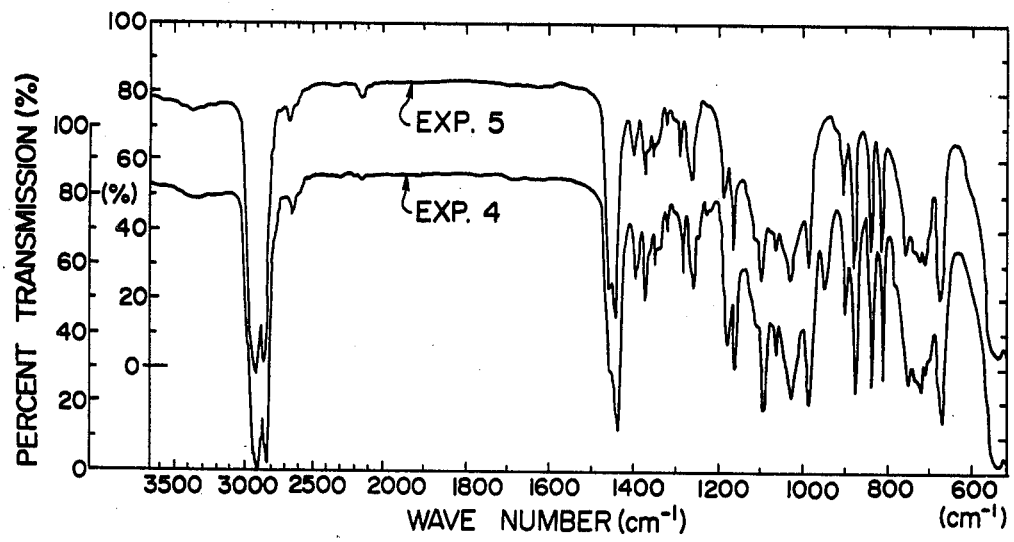
Figure 4:
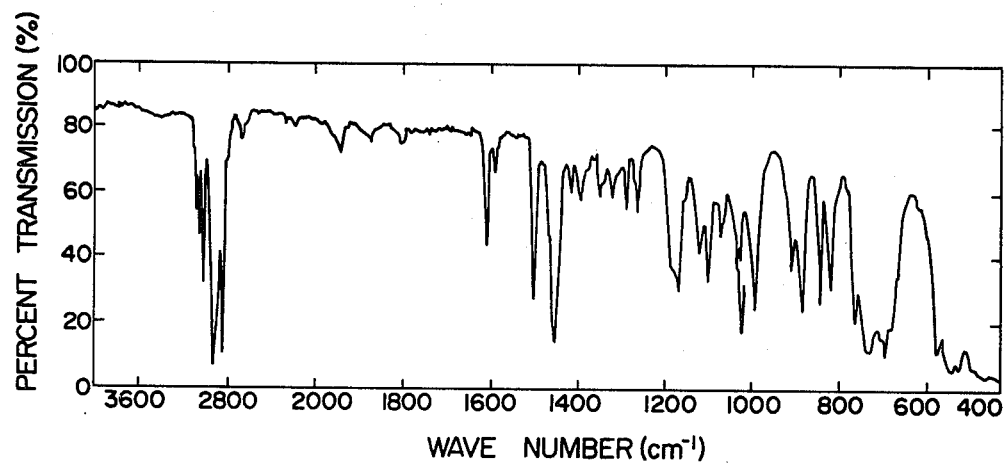
Figure 5:
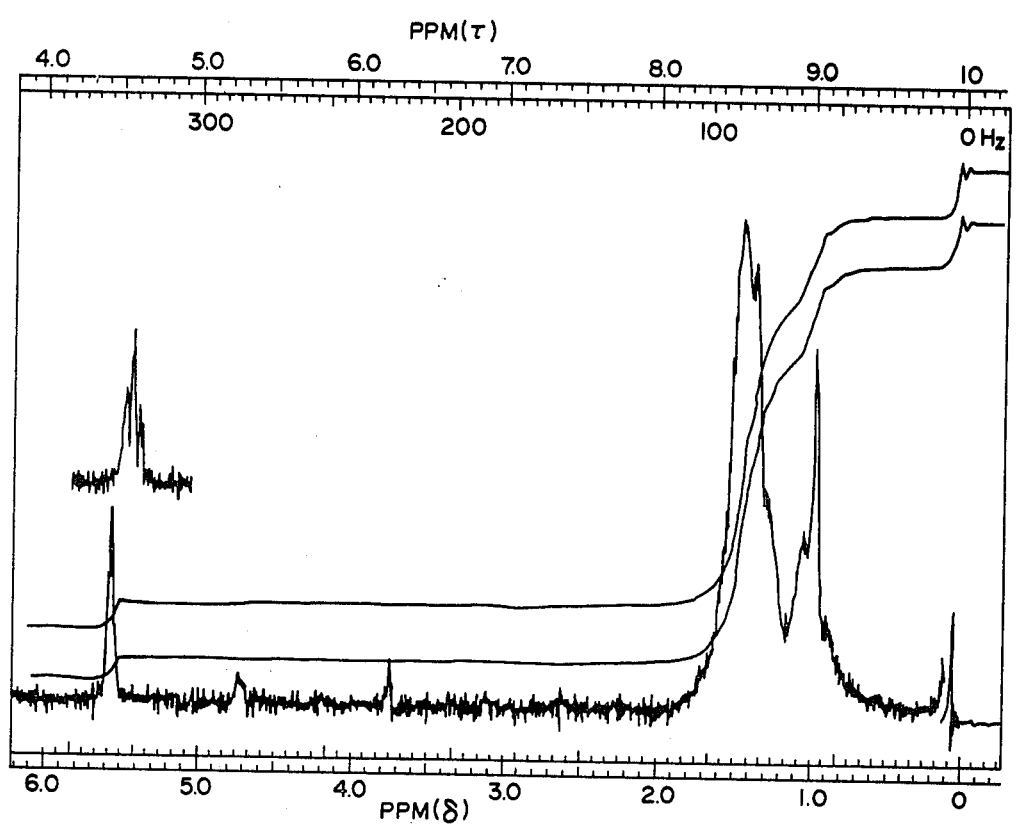
Figure 6:
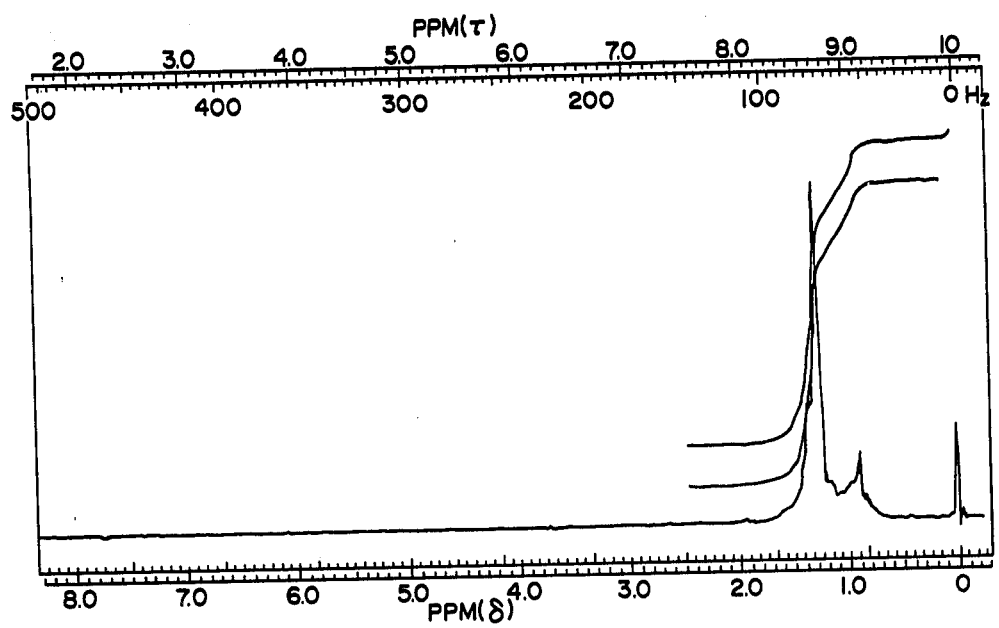
Figure 7:
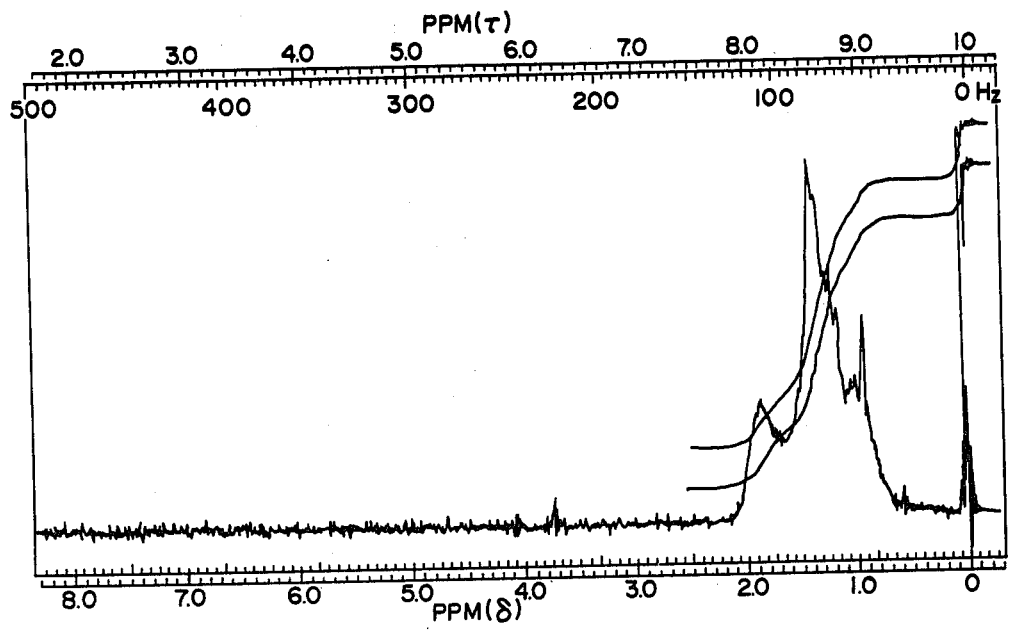
Figure 8:
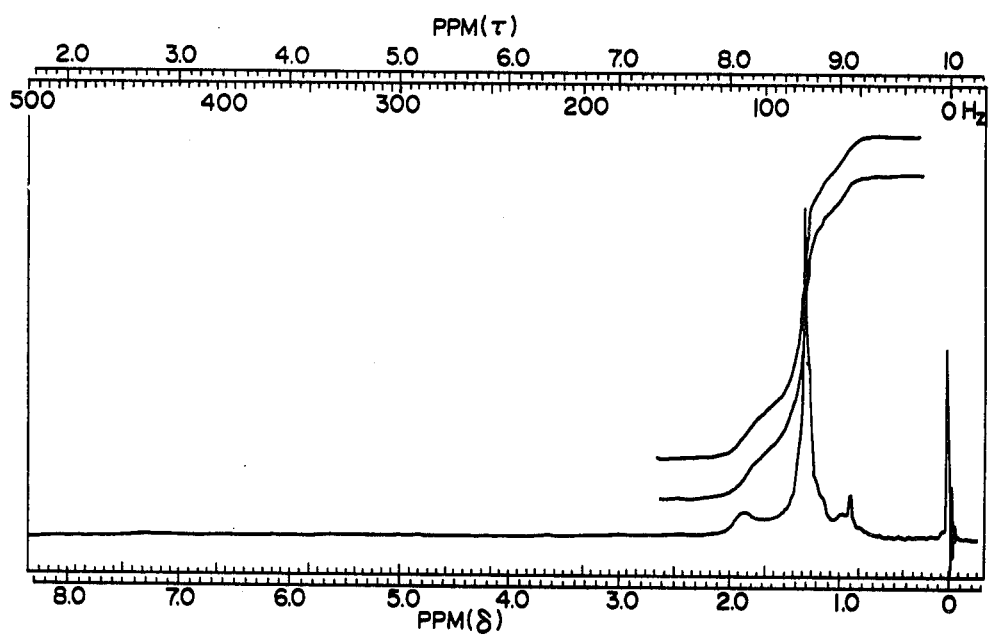
Figure 9:
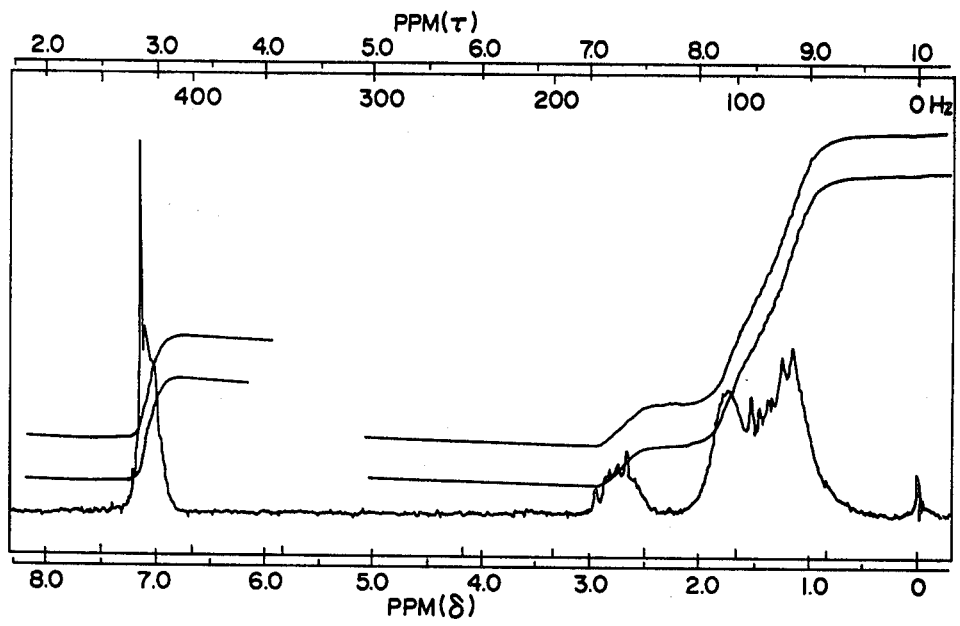

| Example | Compounds | Number of FIGS. |
| --- | --- | --- |
| Example 1 | n-hexyldichlorosilane I.R. | FIG. 1 |
| | n-hexyldichlorosilane N.M.R. | FIG. 5 |
| | n-hexyldodecyldichlorosilane I.R. | FIG. 2 |
| | n-hexyldodecyldichlorosilane N.M.R. | FIG. 6 |
| Example 4 | hexylcyclohexyldichlorosilane I.R. | FIG. 3 |
| | hexylcyclohexyldichlorosilane N.M.R. | FIG. 7 |
| Example 5 | dodecylcyclohexyldichlorosilane I.R. | FIG. 3 |
| | dodecylcyclohexyldichlorosilane N.M.R. | FIG. 8 |
| Example 6 | cyclohexylphenethyldichlorosilane I.R. | FIG. 4 |
| | cyclohexylphenethyldichlorosilane N.M.R. | FIG. 9 |

EXAMPLE 1

Dichlorosilane in an amount of 74.7 g (0.74 mol), 63.0 g of 1-hexane (0.75 mol) and as a catalyst 0.684 g of $RhCl(PPh_3)_3$ ($7.4 \times 10^{-4}$ mol) were charged in a 500 ml pressure proof stainless reaction tube and after sealing, reaction was carried out by heating in an oil bath at a temperature of 90° C. for 13 hours. Then reaction liquid was subjected to vacuum distillation to obtain 110 g (0.59 mol) of n-hexyldichlorosilane. The boiling point of this product was 100°-102° C./100 mmHg and the refractive index $n_D^{20}$ was 1.4412. Further, the infrared spectrum of this product is shown in FIG. 1 indicating characteristic absorptions of Si—H at 2213 $cm^{-1}$. The NMR spectrum of this product is shown in FIG. 5. Thus it was confirmed that the product corresponded to the formula $(n-C_6H_{13})SiHCl_2$.

The above-mentioned n-hexyldichlorosilane in an amount of 3.33 g (18 millimol), 3.36 g (20 millimol) of 1-dodecene and as a catalyst a solution of $H_2PtCl_6 \cdot 6H_2O$ in isopropanol (0.05 mol % relative to dichlorosilane) were charged in a flask equipped with a cooler and the mixture was reacted with stirring in an oil bath at 50° C. for 15 hours. After reaction, reaction solution was distilled to obtain n-hexyldodecyldichlorosilane. The infrared spectrum of this compound is shown in FIG. 2. The absorption of Si—H band at 2213 $cm^{-1}$ vanished. The NMR spectra of this compound is shown in FIG. 6. The formula $(n-C_6H_{13})(n-C_{12}H_{25})SiCl_2$ for this compound was confirmed.

EXAMPLE 2

Dichlorosilane in an amount of 75.8 g (0.75 mol), 228.5 g of 1-dodecene (1.36 mol) and 0.05 mol % of a catalyst $NiCl_2-(PPh_3)_2$ (relative to dichlorosilane) were charged in a 500 ml pressure-proof stainless steel reactor and sealed. A reaction was carried out at 100° C. for 30 hours and the reacted liquid was distilled to obtain n-dodecyldichlorosilane ($n-C_{12}H_{25}SiHCl_2$).

Resultant n-dodecyldichlorosilane in an amount of 161.4 g (0.6 mol), 22.4 g of ethylene (0.8 mol) and a solution of $H_2PtCl_6 \cdot 6H_2O$ in isopropanol (0.05 mol % relative to n-dodecyldichlorosilane) were charged in a pressure-proof stainless steel reactor. After sealing, reaction was carried out at 50° C. for 25 hours to give n-dodecylethyldichlorosilane $[(n-C_{12}H_{25})(C_2H_5)SiCl_2]$.

EXAMPLE 3

Dichlorosilane in an amount of 60.6 g (0.6 mol), 176.4 g of 1-octadecene (0.7 mol) and 0.07 mol % of $RhCl(PPh_3)_3$ (relative to dichlorosilane) were charged in a 500 ml pressure-proof stainless steel reactor. After sealing, reaction was carried out at 130° C. for 30 hours. The reacted liquid was distilled in vacuo to give n-octadecyldichlorosilane ($n-C_{18}H_{37}SiHCl_2$).

Resultant n-octadecyldichlorosilane in an amount of 176.5 g (0.5 mol), 50.4 g of 1-hexane (0.6 mol) and 0.05 mol % of a $H_2PtCl_2 \cdot 6H_2O$ solution in isopropanol (relative to n-octadecyldichlorosilane) were reacted in a flask with stirring at 50° C. for 25 hours to give n-hexyloctadecyldichlorosilane $[(n-C_6H_{13})(n-C_{18}H_{37})SiCl_2]$.

EXAMPLE 4

Dichlorosilane in an amount of 83.5 g (0.827 mol), 82.3 g of cyclohexene (1.00 mol), 0.05 mol % of chloroplatinic acid (relative to dichlorosilane) were charged in a 500 ml pressure-proof stainless steel reactor and after sealing, reaction was carried out by heating in an oil bath at 100° C. for 30 hours. After reaction, the seal of the reactor was broken and the reacted liquid was discharged and subjected to vacuum distillation to obtain 139.3 g (0.761 mol) of cyclohexyldichlorosilane having a boiling point of 110°~112° C./155 mmHg.

This cyclohexyldichlorosilane in an amount of 139.3 g (0.761 mol), 95.1 g of 1-hexene (1.16 mol) and 0.05 mol % of chloroplatinic acid (relative to cyclohexyldichlorosilane) were reacted by heating in an oil bath at 60° C. for 3 hours with stirring. Thereafter 183.5 g (0.69 mol) of hexylcyclohexyldichlorosilane was obtained by vacuum distillation. The yield relative to cyclohexyldichlorosilane was 90.7% and that relative to dichlorosilane was 83.2%. This hexylcyclohexyldichlorosilane had a boiling point of 92°~95° C./1.5 mmHg and a refractive index $n_D^{20}$ of 1.4744. The results of elemental analysis were as follows: measured value, C, 54.28%; H, 9.15%; Cl, 25.6%, theoretical value, C, 53.92%; H$_2$, 9.05%; Cl, 26.83%. Further infrared spectrum is shown in FIG. 3 and NMR spectrum is shown in FIG. 7 and from the above-mentioned result, it was confirmed that the product had a formula $(cyclohexyl)(n-C_6H_{13})SiCl_2$.

EXAMPLE 5

Cyclohexyldichlorosilane obtained as in Example 4, in an amount of 3.30 g (18.0 millimol), 3.37 g of 1-dodecene (20.0 millimol) and 0.05 mol % of chloroplatinic acid (relative to cyclohexyldichlorosilane) were reacted in a flask with stirring in an oil bath at 60° C. for 8 hours. Thereafter by vacuum distillation 5.69 g (16.2 millimol) of dodecylcyclohexyldichlorosilane was obtained. The yield relative to cyclohexyldichlorosilane was 90% and that relative to dichlorosilane was 82.8%.

This dodecylcyclohexyldichlorosilane had a boiling point of 167°~170°/3 mmHg and a refractive index $n_D^{20}$ of 1.4741. The infrared spectrum of this product is shown in FIG. 3 and the NMR spectrum is shown in FIG. 8. From the above-mentioned result, it has been confirmed that the product has a formula (cyclohexyl)(n—$C_{12}H_{25}$)$SiCl_2$.

COMPARATIVE EXAMPLE 1

Dichlorosilane in an amount of 83.5 g (0.827 mol), 88.6 g of 1-hexene (1.08 mol) and 0.05 mol % of chloroplatinic acid (relative to dichlorosilane) were charged in a stainless steel reactor and sealed and subjected to reaction in a bath at a temperature of 50° C. for 5 hours. After reaction, the seal of the reactor was broken and the reacted liquid was discharged, and by vacuum distillation, n-hexyldichlorosilane was obtained with a yield of 18% and di-n-hexyldichlorosilane with a yield of 72%.

This n-hexyldichlorosilane in an amount of 30.5 g (0.165 mol), 17.2 g of cyclohexene (0.21 mol) and 0.05 mol % of chloroplatinic acid (relative to hexyldichlorosilane) were subjected to reaction in a flask with stirring at a temperature of 40° C. for 20 hours. No hexylcyclohexyldichlorosilane was obtained.

EXAMPLE 6

Dichlorosilane in an amount of 5.35 g (53.0 millimol) 5.70 g of styrene (54.7 millimol) and as a catalyst 0.0490 g ($5.3 \times 10^{-5}$ mol) of $RhCl(PPh_3)_3$ were charged into a 100 ml pressure-proof stainless steel reactor and after sealing, reaction was carried out by heating in an oil bath at 80° C. for 20 hours. Thereafter the reacted liquid was subjected to vacuum distillation to obtain 9.5 g (46.3 millimol) of a product having a boiling point of 76°~77° C./3 mmHg and a refractive index $n_D^{20}$ of 1.5199.

The infrared spectrum of the product shows a characteristic absorption of Si—H at 2206 cm$^{-1}$. The NMR spectrum shows signals of Si—H, Si—$CH_2$, $C_6H_5$—$CH_2$— and $C_6H_5$— protons at the peaks of 5.52 ppm, 1.53 ppm, 2.88 ppm and 7.22 ppm, respectively. From the above-mentioned result, it was confirmed that the product was phenethyldichlorosilane.

Then into a 100 ml pressure-proof stainless steel reactor; 6.21 g (30.3 millimol) of the above-mentioned phenethyldichlorosilane, 4.47 g (54.4 millimol) of cylcohexene and 0.1 ml of a chloroplatinic acid solution in isopropanol (0.03 mol % relative to phenethyldichlorosilane) were charged and sealed. Reaction was carried out in an oil bath at 100° C. with stirring for 17.5 hours. After completion of reaction, the reacted solution was subjected to vacuum distillation to obtain 5.30 g (18.4 millimol) of cyclohexylphenethyldichlorosilane. This cyclohexylphenethyldichlorosilane had a boiling point of 112.8°~115.4° C./2.0 mmHg. The infrared spectrum of this compound is shown in FIG. 4. There is no characteristic absorption of Si-H at 2100 cm$^{-1}$. The NMR spectrum is shown in FIG. 9. There are signals of $\delta$ value at 1.0~2.0 ppm (Si—$CH_2$ and C—$CH_2$—); 2.4~3.0 ppm (—$CH_2$—$C_6H_5$) and 7.15 ppm (—$C_6H_5$). The integral ratio thereof was 14:2:5. In the mass spectrum analysis, parent ion was M+ 286.

From the above-mentioned result, it was confirmed that the product had the structure of the formula (III) of cyclohexylphenethyldichlorosilane.

EXAMPLE 7 n-Octadecyldichlorosilane in an amount of 176.5 g (0.5 mol) obtained according to a process same with that of example 3, 33.7 g (0.6 mol) of 1-butene and 0.05 mol % isopropanol solution of $H_2PtCl_6.6H_2O$ (relative to n-octadecyldichlorosilane) were charged in a 500 ml pressure proof stainless steel reaction tube and after sealing the mixture was reacted at 50° C. for 2 hours to produce n-butyloctadecyldichlorosilane [(n—$C_4H_9$)-(n—$C_{18}H_{37}$)$SiCl_2$].

EXAMPLE 8

Dichlorosilane in an amount of 76.3 g (0.76 mol), 33.6 g (0.8 mol) of propylene and 0.1 mol % (relative to dichlorosilane) of $RuH_2(PPh_3)_4$ were charged in a 500 ml pressure proof stainless steel reactor and sealed. After the reaction at 100° C. for 5 hours, the reacted solution was distilled to obtain n-propyldichlorosilane [(n—$C_3H_7$)$SiHCl_2$].

Resulting n-propyldichlorosilane in an amount of 57.2 g (0.4 mol), 84.2 g (0.5 mol) of 1-dodecene and 0.05 mol % (relative to n-propyldichlorosilane) of a $H_2PtCl_6.6H_2O$ isopropanol solution were reacted in a flask with stirring at 50° C. for 5 hours to produce n-propyldodecyldichlorosilane [(n—$C_3H_7$)(n—$C_{12}H_{25}$)$SiCl_2$].

What is claimed is:

1. A disubstituted dichlorosilane having the general formula

(I)

wherein R' is an alkyl group having 2~3 carbon atoms and R" is an alkyl group having 8~20 carbon atoms, or R' is an alkyl group having 4~20 carbon atoms and R" is an alkyl group having 5~20 carbon atoms which is different from R', or R' is phenethyl group and R" is cyclohexyl group.

2. A disubstituted dichlorosilane having the general formula

(I)

defined in claim 1 wherein R' is alkyl group having 2 or 3 carbon atoms and R" is alkyl group has 8~20 carbon atoms.

3. A disubstituted dichlorosilane having the general formula

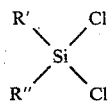  (I)

defined in claim 1 wherein R' and R" are different alkyl groups and R' has 4~20 carbon atoms and R" has 5~20 carbon atoms.

4. A disubstituted dichlorosilane defined in claims 3 wherein the difference of number of carbon atoms of R' and R" is 6 or more.

5. A disubstituted dichlorosilane defined in claim 1 having the general formula

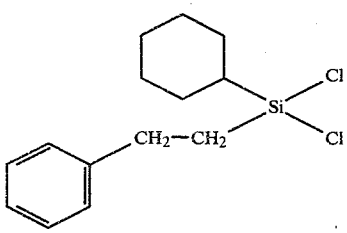

6. Disubstituted dichlorosilanes as set forth in claim 1 which are produced by reacting dichlorosilane with an α-olefin or styrene in the presence of a homogenous complex catalyst selected from the group consisting of RhH(PPh$_3$)$_4$, RhCl(CO)(PPh$_3$)$_3$, RhCl(PPh$_3$)$_3$, RuCl$_2$(PPH$_3$)$_3$, RuHCl(PPh$_3$)$_3$[C$_6$H$_6$], RuH$_3$(PPh$_3$)$_3$[Si(OCH$_3$)$_3$], RuH$_3$(PPh$_3$)$_3$ [Si(OCH$_3$)$_2$Pt], RuH(PPh$_3$)$_3$[Si(C$_2$H$_5$)$_2$Cl], RuH$_2$(PPh$_3$)$_4$, NiCl$_2$(PPh$_3$)$_2$, PdCl$_2$(PPh$_3$)$_2$, and Pt(PPh$_3$)$_4$, wherein Ph stands for a phenyl group, to form a monosubstituted dichlorosilane having the general formula R°HSiCl$_2$ (wherein R° is an alkyl having 2–20 carbon atoms, or phenethyl) and reacting said monosubstituted dichlorosilane with an α-olefin having carbon atoms of 2 to 20 (but different from the number of carbon atoms of R°) or cyclohexene (excepting the case where R° is alkyl) in the presence of chloroplatinic acid at a temperature of 30°–150° C.

7. Disubstituted dichlorosilanes having the general formula

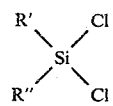  (I)

wherein R' is an alkyl group having 2 or 3 carbon atoms and R" is alkyl group having 8–20 carbon atoms which are produced by reacting dichlorosilane and ethylene or propylene in the presence of the catalyst of claim 6 at a temperature of 30°–200° C. for 0.1 to 60 hours to produce ethyldichlorosilane or propydichlorosilane compound and reacting said monosubstituted dichlorosilane with an α-olefin compound having 8–20 carbon atoms.

8. Disubstituted dichlorosilanes having the general formula

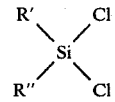  (I)

wherein R' is an alkyl group having 2 or 3 carbon atoms and R" is an alkyl group having 8–20 carbon atoms which are produced by reacting dichlorosilane and an α-olefin compound having 8–20 carbon atoms in the presence of the catalyst of claim 6 at a temperature of 30°–200° C. for 0.1–60 hours to produce monoalkyldichlorosilane and said monosubstituted dichlorosilane is reacted with ethylene or propylene.

9. Disubstituted dichlorosilanes having the general formula

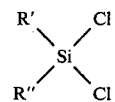  (I)

wherein R' and R" are different alkyl groups and R' has 4–20 carbon atoms and R" has 5–20 carbon atoms which are produced by reacting a dichlorosilane with an α-olefin compound having 4–20 carbon atoms in the presence of the catalyst of claim 6 at a temperature of 30°–200° C. for 0.1–60 hours to produce a monosubstituted dichlorosilane compound with an α-olefin compound having 5 to 20 carbon atoms, but different numbers of carbon atoms from said monoalkyl substitute.

10. Disubstituted dichlorosilanes having the general formula

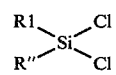  (I)

wherein R' and R" are different alkyl groups and R' has 4–20 carbon atoms and R" has 5–20 carbon atoms produced by reacting a dichlorosilane and an α-olefin compound having 5–20 carbon atoms in the presence of the catalyst of claim 6 at a temperature of 30°–200° C. for 0.1–60 hours to produce a monoalkyldichlorosilane having 5 to 20 carbon atoms and the resulting monoalkyldichlorosilane is reacted with butene.

11. Cyclohexylphenethydichlorosilane having the general formula

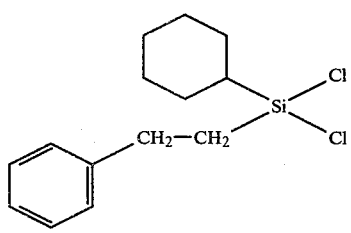

which is produced by reacting a dichlorosilane and styrene in the presence of the catalyst of claim 6 at a temperature of 30°–150° C. for 0.1–60 hours to produce a monophenethyldichlorosilane and reacting said monosubstitute with cyclohexene at a temperature of 80°–150° C. for 5–20 hours.

* * * * *